US008440221B2

(12) United States Patent
Zumbrunn et al.

(10) Patent No.: US 8,440,221 B2
(45) Date of Patent: May 14, 2013

(54) TRANSDERMAL DRUG DELIVERY METHOD AND SYSTEM

(75) Inventors: Werner Zumbrunn, Muttenz (CH); Hans Werner Van de Venn, Winterthur (CH); George Imanidis, Binningen (CH); Guy DiPierro, Hamilton, NJ (US)

(73) Assignee: Chrono Therapeutics, Inc., Cambridge, MA (US)

( * ) Notice: Subject to any disclaimer, the term of this patent is extended or adjusted under 35 U.S.C. 154(b) by 1075 days.

(21) Appl. No.: 10/711,389

(22) Filed: Sep. 15, 2004

(65) Prior Publication Data

US 2005/0238704 A1 Oct. 27, 2005

Related U.S. Application Data

(63) Continuation of application No. PCT/IB2004/002947, filed on Sep. 13, 2004.

(30) Foreign Application Priority Data

Oct. 27, 2003 (CH) ...................................... 1833/03

(51) Int. Cl.
*A61K 9/70* (2006.01)
(52) U.S. Cl.
USPC ......................................................... 424/449
(58) Field of Classification Search .................. None
See application file for complete search history.

(56) References Cited

U.S. PATENT DOCUMENTS

| 4,379,454 A | 4/1983 | Campbell et al. |
| 4,545,990 A | 10/1985 | Le Foyer de Costil et al. |
| 4,708,716 A | 11/1987 | Sibalis |
| 4,917,895 A | 4/1990 | Lee et al. |
| 5,242,941 A | 9/1993 | Lewy et al. |
| 5,273,756 A | 12/1993 | Fallon et al. |
| 5,352,456 A | 10/1994 | Fallon et al. |
| 5,370,635 A | 12/1994 | Strausak et al. |
| 5,389,679 A | 2/1995 | Alliger |
| 5,405,614 A | 4/1995 | D'Angelo et al. |
| 5,505,958 A | 4/1996 | Bello et al. |

(Continued)

FOREIGN PATENT DOCUMENTS

| CA | 2142871 | 3/1994 |
| JP | 2202813 | 8/1990 |
| WO | 03/022349 A2 | 3/2003 |

OTHER PUBLICATIONS

International Preliminary Report on Patentability; PCT/IB2004/002947; May 1, 2006.

(Continued)

*Primary Examiner* — Anand Desai
*Assistant Examiner* — Melissa Mercier
(74) *Attorney, Agent, or Firm* — Foley & Lardner LLP

(57) ABSTRACT

The invention concerns a transdermal delivery system for controlled dispensing of an active substance to and through a porous surface. A certain amount of fluid comprising at least one active substance and at least one solvent is dispensed into an administration reservoir. In the administration reservoir the at least one solvent is separated from the administration reservoir by a solvent recovery means such that the active substance achieves a certain level on an interface device which is permeable for the one active substance. Thereby the active substance is absorbable via diffusion from the interface device by a porous surface to be treated.

25 Claims, 4 Drawing Sheets

U.S. PATENT DOCUMENTS

Figure 1:
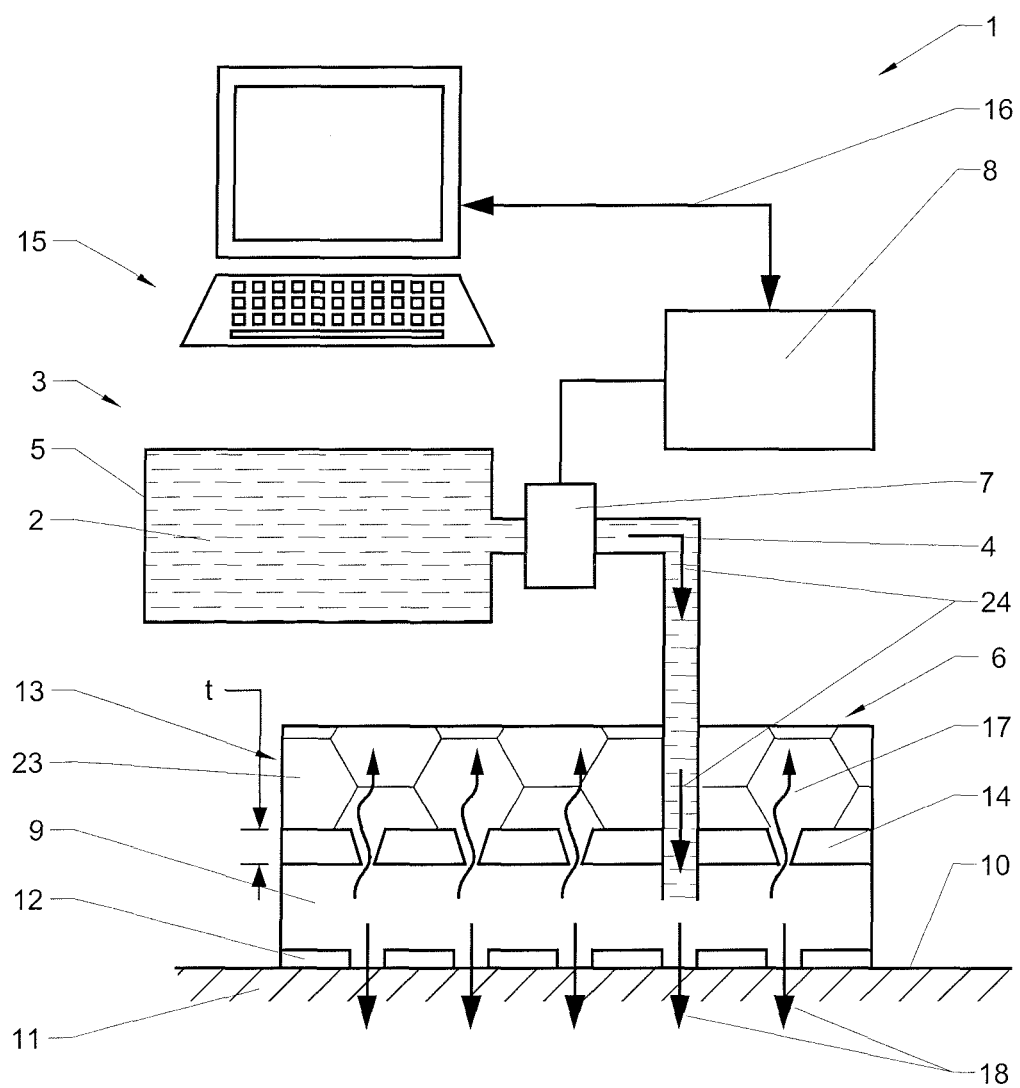

| | | | |
|---|---|---|---|
| 5,538,503 A * | 7/1996 | Henley | 604/20 |
| 5,616,332 A | 4/1997 | Herstein | |
| 5,785,688 A | 7/1998 | Joshi et al. | |
| 5,820,875 A | 10/1998 | Fallon et al. | |
| 5,879,322 A | 3/1999 | Lattin et al. | |
| 5,932,240 A | 8/1999 | D'Angelo et al. | |
| 5,993,435 A * | 11/1999 | Haak et al. | 604/501 |
| 6,068,853 A | 5/2000 | Giannos et al. | |
| 6,129,702 A | 10/2000 | Woias et al. | |
| 6,165,155 A | 12/2000 | Jacobsen et al. | |
| 6,211,296 B1 * | 4/2001 | Frate et al. | 525/207 |
| 6,214,379 B1 | 4/2001 | Hermelin | |
| 6,374,136 B1 * | 4/2002 | Murdock | 604/20 |
| 6,539,250 B1 | 3/2003 | Bettinger | |
| 6,595,956 B1 | 7/2003 | Gross et al. | |
| 6,638,528 B1 | 10/2003 | Kanios | |
| 6,723,077 B2 | 4/2004 | Pickup et al. | |
| 6,723,086 B2 | 4/2004 | Bassuk et al. | |
| 6,861,066 B2 | 3/2005 | Van de Casteele | |
| 6,867,342 B2 | 3/2005 | Johnston et al. | |
| 6,887,202 B2 | 5/2005 | Currie et al. | |
| 2002/0127256 A1 | 9/2002 | Murad | |
| 2003/0065294 A1 * | 4/2003 | Pickup et al. | 604/304 |
| 2004/0138074 A1 | 7/2004 | Ahmad et al. | |
| 2005/0034842 A1 | 2/2005 | Huber et al. | |
| 2005/0182307 A1 | 8/2005 | Currie et al. | |
| 2005/0238704 A1 | 10/2005 | Zumbrunn et al. | |

OTHER PUBLICATIONS

The Science and Practice of Pharmacy, 19$^{th}$ Ed., p. 1582-1584, (1995).

L. Molander et al., "Reduction of Tobacco Withdrawl Symptons with a Sublingual Nicotine Tablet: A Placebo Controlled Study," Nicotine & Tob. Res., 2000, 2, pp. 187-191.

Shin et al., Enhanced Bioavailability of Triprolidine from the Transdermal TPX Matrix System in Rabbits, *Intern. Journ. of Pharm.*, 234, pp. 67-73 (2002).

Office Action for related U.S. Appl. No. 11/162,525 dated Feb. 19, 2009.

Office Action for related U.S. Appl. No. 11/162,525 dated Aug. 27, 2009.

Office Action for related U.S. Appl. No. 10/711,389 dated Jul. 1, 2009.

Office Action for related U.S. Appl. No. 11/083,178 dated Oct. 2, 2009.

Office Action for related U.S. Appl. No. 11/981,672 dated Oct. 7, 2009.

Office Action cited in related U.S. Appl. No. 11/162,525, dated Feb. 5, 2010.

Office Action cited in related U.S. Appl. No. 11/162,517, dated Nov. 24, 2009.

Prosise et al., (Effect of abstinence from smoking on sleep and day time sleepiness), *Amer. College of Chest Physicians*, vol. 105, pp. 1136-1141 (1994).

Notice of Allowance cited in related U.S. Appl. No. 11/162,525, dated Apr. 26, 2010.

U.S. Office Action cited in related U.S. Appl. No. 11/162,517, dated Jun. 3, 2010.

U.S. Office Action cited in related U.S. Appl. No. 11/981,672, dated Mar. 23, 2009.

Benzoyl Peroxide: "Enhancing Antibiotic Efficacy in Acne Management," http://www.skintherapyletter.com/2010/15.10/2.html, Nov. 2010, pp. 1-8, Accessed May 18, 2011.

Notice of Allowance cited in related U.S. Appl. No. 11/981,672, dated Mar. 2, 2012.

Office Action cited in related U.S. Appl. No. 11/981,672, dated Nov. 10, 2011.

Office Action cited in related U.S. Appl. No. 11/981,672, dated Apr. 4, 2011.

Office Action cited in related U.S. Appl. No. 11/083,178, dated Jan. 26, 2012.

Office Action cited in related U.S. Appl. No. 11/083,178, dated May 27, 2011.

Office Action cited in related U.S. Appl. No. 12/835,693, dated Aug. 1, 2012.

Office Action cited in related U.S. Appl. No. 11/162,517, dated Nov. 19, 2012.

Office Action cited in related U.S. Appl. No. 12/835,693, dated Dec. 20, 2012.

* cited by examiner

TRANSDERMAL DRUG DELIVERY METHOD AND SYSTEM

The present application is continuation of PCT Application No. PCT/IB2004/002947 filed on Sep. 13, 2004 entitled Transdermal Drug Delivery Method and System, the specification of which is incorporated herein by reference, which claims priority to Swiss Patent Application No. 01833/03 Filed on 27 Oct. 2003.

FIELD OF THE INVENTION

The invention concerns a delivery system for a chemical substance for the controlled dispensing of the chemical substance to and through a surface, respectively skin. More specifically the invention relates to a method and a system usable, i.e. for transdermal drug delivery.

BACKGROUND OF THE INVENTION

Delivery of chemical substance to and through a surface administrated over a desired time is a subject matter in different areas. A very important subject area, where the delivery of chemical substances to or through a permeable surface is important, is medicine. Although the invention is not restricted to the field of medicine the invention is described in the following mainly with respect to this field of application.

Pharmaceutical substances provide effective treatments for a variety of illnesses. In general it is necessary that medication is applied at a certain time or with a certain time pattern or it is necessary to keep the level of medication at a certain value to achieve the aimed therapeutic result most efficiently. Unfortunately patients often fail to take their medications at the proper prescribed intervals or period of time. Moreover there are drugs, which are partially or totally inactivated following oral ingestion, by the highly acidic environment of the stomach or by the filter impact of the liver.

In order to overcome such problems, drugs are administered by transdermal delivery. The most common parenteral methods (methods avoiding digestion) for drug delivery are the administration in separate dosages by injections with a needle or continuously by drip. For a long term treatment these methods may be uncomfortable for the patient because of the repeated injury by needle injections and the limited liberty of action due to intravenous drip apparatus.

A more comfortable method for drug delivery utilizes patches which are applied on the surface of the skin. Patches are known since more than twenty years; i.e. the product TransdermScop® of Novartis has been on the market since 1981. Those patches are portable and therefore very comfortable and furthermore very suitable for patients which are scared by needles and cannulae. Examples of drugs that are routinely administered by skin applied patches are nicotine, steroid hormones, and some analgesics (such as fentanyl). Using plaster-like patches for drug delivery provides continuous dosages usually over a relatively short period of time (such as a day up to a week), without requiring active participation of the patient.

In order to provide a more flexible, precise and complex administration of drugs by a patch based system over a certain period of time, portable dispensing systems have been developed in the last few years which are connectable or connected in a fixed way to a patch. These systems in general comprise a dispensing system with a reservoir for a drug. In case of more than one reservoir the reservoirs are provided for one drug or different drugs or different components of a drug. Further the dispensing system has a dispensing unit. The reservoir and the dispensing unit are interconnected to the patch. Different types of dispensing units are known from prior art.

U.S. Pat. No. 5,785,688 (Joshi, et al.) discloses an apparatus for subcutaneous drug delivery having a fluid reservoir disposed within a housing for storing the fluid, a pump or pressurized chamber for pressurizing a driving gas is foreseen for exerting a force on the fluid reservoir to expel the fluid reservoir's contents. A needle or absorbent pad are interconnected with the reservoir.

U.S. Pat. No. 5,405,614 (D'Angelo, et al.) discloses a drug delivery system for transdermal delivery of drugs through the skin. The delivery system comprises a container for containing the drug with a drug release opening. An ultrasonic transducer is disposed in the general conduit area for generating ultrasonic waves aimed at the skin area.

U.S. Pat. No. 5,932,240 (D'Angelo, et al.) describes a patch-like multidose transdermal drug delivery system having a laminate composite with a plurality of compartments. Each compartment is a reservoir for a unit dose of a drug active to be transdermally administered. Individual seals are removable to release a unit dose of drug into contact with the skin of a patient.

U.S. Pat. No. 6,723,077 (Pickup et al.) is directed to a jet dispenser using inkjet technology for delivery of bioactive agents. The dispenser propels a certain volume of bioactive agent directly towards the skin, where they exert a local or topical effect, or move through the skin for transdermal systemic delivery. Drugs are either delivered directly to the skin, or are introduced into a transdermal patch, which may receive repeated dosages. A controller in the dispenser controls delivery and timing of drug administration. Due to the direct application of the active substance to the skin the process of medication is difficult to control and mainly determined by the diffusion rate of the skin.

U.S. Pat. No. 6,165,155 (Jacobsen, et al.) discloses an automatic drug delivery system utilizing a control pad coupled to a disposable drug storage and delivery system. Expanding propellant gas exerts pressure on a drug in a chamber and forces it from the storage reservoir. Drug delivery is based upon a hypodermic needle, a jet nozzle injecting the drug into a subcutaneous tissue or a patch for passive transdermal delivery or iontophoretic transdermal diffusion.

U.S. Pat. No. 4,917,895 (Lee, et al.) describes a diffusional drug with a metal layer and activating means which are inert when dry. The system is activated by moisture whereby the activating means provide release of an eroding agent which erodes the metal layer through which the therapeutic agent diffuses and is subsequently delivered.

U.S. Pat. No. 4,379,454 (Campbell, et al.) discloses a one-way skin patch with a top backing layer, a drug reservoir, a diffusion membrane and a contact adhesive layer. The backing layer defines the top of the patch and is made from a material or combination of materials that is substantially impermeable to the components contained in the drug reservoir. The diffusion membrane is made of a dense or microporous polymer film that is permeable for the drug and the enhancer. The patch coadministers a drug and a percutaneous absorption enhancer to a defined area of the skin. The drug is provided to a basal surface at a rate at least as great as the rate at which the skin is able to absorb the drug whereas the enhancer is via a rate controlling means at a substantially constant rate that increases the permeability of the treated area of skin to the drug to a level at which the drug is absorbed at a therapeutically effective rate.

U.S. Pat. No. 4,708,716 (Sibalis) describes a transdermal drug applicator for administration of drugs through the skin into the blood stream of a patient. The drug applicator embodies a plurality of reservoirs for containing the medicament. A battery is disposed adjacent to one side of the reservoirs. When the applicator is adhered to and mounted on the skin a complete electrical circuit through the skin is formed and the medicament in the reservoir migrates out of the reservoir and through the skin into the patient's blood stream.

U.S. Pat. No. 6,129,702 (Woias, et al.) describes a medicament dosing system which is based on overpressure. The medicament dosing system comprises a replaceable and a permanent unit. The replaceable unit has a fluid reservoir for receiving a medicament in liquid form. The permanent unit comprises valve and control means which are coupled to a temperature sensor and the valve so as to control a flow rate of the liquid medicament by clocked actuation the valve depending on the temperature detected.

U.S. Pat. No. 5,273,756 (Fallon, et al.) is directed to a transdermal drug delivery device using a microporous membrane to achieve delayed onset. The transdermal drug delivery device comprises a layered setup with a pressure rupturable layer. The device is made such that it initially takes at least about six hours for the drug to diffuse to the skin from the reservoir once the reservoir is ruptured.

U.S. Pat. No. 5,505,958 (Bello, et al.) describes a one-way transdermal drug delivery device which has a drug-storing matrix made out of a flexible cellular structure fabricated from a flexible cellular thermoplastic for storing at least one drug.

U.S. Pat. No. 5,879,322 (Lattin, et al.) is directed to a self-contained transdermal drug delivery device by electro transport means with electrodes designed to be worn on the skin. The electro transport device can be used by patients to deliver a drug during a prescribed course of therapy, e.g. the delivery of an analgesic to control pain.

CA2142871 (Miranda, et al.) discloses a one-way transdermal drug delivery device in the form of a laminated composite which delivers a drug continuously over approximately 16 hours, especially in case of problems such as drug tolerance (e.g., nitroglycerin) or sleep disorders (e.g., nicotine). The drug is loaded in the device in a concentration such that the drug becomes depleted from the device after approximately 16 hours to the extent that the rate of delivery of the drug to the patient is slowed to such an extent that the pharmacological effect of the drug on the patient becomes substantially nonexistent.

PCT/GB02/04064 (Watmough, et al.) describes an apparatus which utilises megahertz ultrasound from a piezoelectric transducer to produce liquid jets which penetrate into or through porous media such as animal skin and egg shells. A device in the form of a gun is described that is suitable to receive cartons of drug. A cloud of drops can be driven towards or into the nose or mouth of a patient using a suitable fan or pipework.

It has been tried to accelerate the diffusion rate of an active substance through the skin by various measures, i.e. applying an electric field, ultrasonic, radiation, heat or chemical accelerators. However, all these measures, by exception of chemical accelerators, require much auxiliary power or are technically very complex and expensive. Chemical accelerators often increase the probability of skin irritations, allergic reactions, inflammation and/or swelling.

The efficiency of transdermal drug delivery systems using patches depends often on the diffusion rate of the active substance through the skin, which on one hand depends on the active substance and its solvent and on the other hand varies in a wide range from mammal to mammal even within the same species, thus as from human being to human being, and also from the body area the patch is applied to. The constructions of the patches known from prior art usually try to control these dependencies by a set up of several layers. One important layer is an active substance reservoir or a Polymer-Matrix, in which the active substance is embedded, either dissolved in a solvent or embedded in micro capsules. The reservoir for the active substance is covered with an upper-layer which protects the patch against the environment. The upper-layer has to be impermeable to the active substance and the solvent as well as to substances acting from outside. Two layers may be arranged between the active substance reservoir and the skin: The first layer is a membrane, which is arranged directly adjacent to the active substance reservoir, and the second is an adhesive layer to be patched on the skin which is, if appropriate, covered by a removable protection film before use.

In systems known from prior art the membrane adjacent to the active substance reservoir controls the dispensing of the active substance to the skin. The dispensing rate of the active substance into the skin is mainly influenced by the permeability of the membrane and the concentration. Therefore, to obtain controllable results the permeability of the membrane is chosen such that the diffusion rate of the active substance from the reservoir through the membrane and through the skin into the body is defined mainly by the permeability of the membrane and not by the diffusion rate of the active substance through the skin. The absence of an appropriate membrane would result in very different transport rates of the active substance into the body, because of the different skin characteristics. High diffusion characteristics of the skin imply the risk of an overdose, whereas low diffusion characteristics imply the risk of no therapeutic effect. In order to minimize said problems the permeability of the membrane in some systems has been chosen much lower than the permeability of the different skin types. However, in this case the amount of active substance which diffuses through a specific skin area is much less than the theoretical maximum given by the characteristics of the skin. Hence the size of the patch has to be chosen much bigger than intrinsically necessary.

Patch based delivery systems which are able to effectively administrate the delivery of an active substance to a subject over a certain period of time in precise doses, e.g. delivered at predetermined intervals, are a problem that has not been solved by now. Turning delivery on and off may cause uncontrolled time lag in the delivery rate of the on and off events and leads often over the long term run to a constantly diminishing diffusion rate through the skin.

Most drugs used today perform better therapeutically when delivered in a modulated rather than in a continuous fashion throughout the applied period of time, for example, a circadian rhythm. A number of chemicals are, e.g., needed only at a certain time during the day. Therefore it is necessary to be able to precisely control and apply drugs according to predetermined rules. Currently no technology that is non invasive, does not need an extensive power supply and can be independently used by the targeted individual, such as customer and/or patient is available affording automated control of drug delivery in real time.

It is an object of the present invention to provide a delivery system for an active substance which avoids the draw backs known from the prior art. It is a further object of the present invention to provide a patch based delivery system for an active substance which is able to administrate the delivery of a chemical substance to a subject over a period of time in a controllable way.

SUMMARY OF THE INVENTION

According to the present invention an active substance (drug) normally is dissolved in a fluid solution comprising a solvent. The active substance and/or the solvent are dispensed directly or indirectly via at least one interface device on a porous surface, e.g. skin, such that the active substance is absorbed through or by the porous surface primarily by diffusion.

A device according to the present invention in general comprises dispensing means, e.g. a pump, at least one drug reservoir, at least one administration element (patch reservoir, administration reservoir, administration compartment, administration chamber) and at least one solvent removal and/or recovery element and if necessary control means interconnected to each other. In a preferred embodiment of the invention the administration reservoir and the solvent recovery means are incorporated in an administration unit (patch). The at least one drug reservoir contains a sufficient amount of one or more active substance dissolved or dispersed at an appropriate concentration in a formulation which may contain a solvent or a solvent mixture that is volatile. If appropriate other excipients, for example tissue permeation promoters (enhancers), thickening substances, solubilizers, buffers, chemical stabilizers, preservatives are present too.

The active substance may be any dispensable fluid (for example a liquid, gel or powder), although liquids are particularly of use in the dispensing unit. In some embodiments, at least one of the reservoirs may contain an active substance in powder or other dry form. The powder or other agent is dispensed from the reservoir, and may be combined with a solvent and/or another liquid such as a penetration enhancer. If appropriate the dispensing unit may allow chemical reactions to occur, e.g. in the administration reservoir, as well as phase changes to stabilize (such as a change from a solid to a liquid state).

Examples of active substances which can be administered by the device according to the present invention include pharmaceutical compositions that are capable of transdermal delivery. Such agents include drugs having sufficient lipophilicity or hydrophilicity to move through the skin surface and stratum corneum. Certain of these agents are designed to reach the microvasculature of the skin, for subsequent systemic absorption and distribution. Examples of agents that are suitable for transdermal delivery include scopolamine, nitrates such as nitroglycerine, an antihypertensive or antiadrenergic drug such as clonidine, steroid hormones such as 17-beta-estradiol and testosterone, analgesics, such as the opioid analgesic fentanyl, and treatments for nicotine withdrawal, such as nicotine. Many analogues of these drugs retain their biological activity, and are also suitable for transdermal delivery. Although the disclosed dispensing unit is particularly suited for transdermal delivery of drugs, it can also be used for topical surface application of drugs, such as antibiotics, corticosteroids, minoxidil or retinoids (such as Retin A). For example it is also possible that an active substance, e.g. an insoluble drug, may be encapsulated in a nanoparticular form dispersed in a solvent.

A device according to the present invention may comprise several reservoirs for active substances comprising the same or different agents, for example different agents that combine before or at the time of delivery to modify one or both of the agents, or to produce a desired effect. An example of a modifying substance that may be combined at the point of application is a enhancer that improves cutaneous penetration of the at least one active substance. Penetration enhancers that may be mixed with a bioactive agent at the time of delivery may include solvents such as water; alcohols (such as methanol, ethanol and 2-propanol); alkyl methyl sulfoxides (such as dimethyl sulfoxide, decylmethyl sulfoxide and tetradecylmethyl sulfoxide); pyrrolidones (such as 2-pyrrolidone, N-methyl-2-pyrroloidone and N-(2-hydroxyethyl)pyrrolidone); laurocapram; and miscellaneous solvents such as acetone, dimethyl acetamide, dimethyl formamide, and tetrahyrdofurfuryl alcohol. Other penetration enhancers include amphiphiles such as L-amino acids, anionic surfactants, cationic surfactants, amphoteric surfactants, nonionic surfactants, fatty acids and alcohols. Additional penetration enhancers are disclosed in Remington: The Science and Practice of Pharmacy, 19.sup.th Edition (1995) on page 1583. Of course agents such as penetration enhancers can also be premixed with the bioactive agent prior to the point of application, for example the bioactive agent and modifying substance can be present together in a reservoir.

U.S. Pat. No. 6,723,077 (from now on US'077), already mentioned above, is directed to an applicator for cutaneous delivery of a bioactive composition using a jet dispenser, such as a piezoelectric or thermal jet dispenser, for instance of a construction used in the inkjet printing arts. In difference to US'077 the present invention uses at least one solvent which is at least partially separated during administration of the at least one active substance by a solvent recovery means. A major disadvantage of the piezo electric or thermal jet dispenser described in US'077 is that the bioactive composition is stressed due to heat and/or high pressure which inevitably may occur while application.

In operation the formulation contained in the at least one drug reservoir is dispensed by the dispensing unit into the at least one administration reservoir (patch reservoir). Volume and frequency of administration of the active substance are controlled by a control unit which preferably is freely programmable according to given needs. The solvent recovery means reclaim solvent that was dispensed together with the formulation into the patch reservoir and is not absorbed. The preferably volatile solvent evaporates from the interface continuously and is guided to the solvent recovery means. If appropriate a heating element or other helping means may be used for supporting evaporation of the solvent. However the temperature of the skin in general is sufficient. The solvent recovery means serve to remove depleted solvent from the interface such that, e.g. after repeated dispensing, active substance concentration maintains at a certain concentration and no unwanted substance is accumulated within the device. Upon quitting dispensing of formula, the residual solvent is recovered and dryness of the interface is achieved, which results in controlled termination of drug delivery. Alternatively or in addition depleted solvent may be discharged into environment only, e.g. by direct evaporation.

In general the active substance is completely enclosed in the administration/patch reservoir and is not in contact with the environment or other components. The interface may comprise a membrane (polymer membrane) which may be lined with an absorbent material, such as blotting paper, suitable to receive active substance and facing inwards to the interior of the device. The membrane of the interface is in functional contact with the surface to be treated. The drug formulation is dispensed onto the interface by the dispensing unit which is interconnected to the drug reservoir. The solvent recovery means are normally arranged at a certain distance from the absorbent material preventing uncontrolled absorption of solvent. The volume and frequency of dispensing are freely programmable and are used to control the delivery rate and the time pattern of delivery of the drug.

Due to the reason that an organism in general does not show a steady sensibility with respect to a certain drug and to avoid tolerances against a certain drug the present invention foresees, if appropriate, a non-constant administration of at least one drug over a certain period of time or intervals of time.

Because of that it is possible to avoid an increasing need of active substance to achieve a certain result. By administering an active substance adjusted to the circadian rhythm the result of therapy may be increased significantly. Depending on the field of application and embodiment the present invention offers the opportunity to precisely administer at least one active substance according to a preset or real-time regime. This method is applicable e.g. to reduce the addiction to nicotine or other drugs.

Drug is delivered from the interface primarily by diffusion. The solvent recovery element reclaims the solvent that was dispensed with the formulation onto the interface and was not absorbed otherwise. The solvent recovery element preferably is located within the device and comprises one or more desiccants and/or general adsorbents such as silica gel, molecular sieves or active carbon. These materials are normally arranged within a bag consisting of non-wettable but vapor permeable material e.g. such as GoreTex®. In a preferred embodiment the solvent recovery element is arranged close to but in non-contact with the interface. The volatile solvent evaporates from the interface continuously under the influence of body heat and the vapors are trapped in the solvent recovery element. The solvent recovery element serves the purpose of removing depleted solvent from the interface so that, after repeated dispensing, drug concentration maintains its highest value and no freely moving liquid is formed within the device. Upon quitting dispensing of drug formula, the residual solvent is recovered and dryness of the interface is achieved, which brings about stoppage of drug delivery. The solvent recovery element is contained in a non-wettable material in order to avoid uptake of drug formula and consequent loss of drug.

Several parameters are relevant for the amount of active substance absorbed by the surface to be treated such as concentration of the active substance in the solvent, the repetition-rate of supply and the volume supplied. These parameters are controllable by the described invention.

Solvent that is not absorbed by the skin in a sufficient way is carried off in another way than by absorption through the skin, e.g. by evaporation into the environment and/or by absorption by another means, e.g. absorbing substance such as silica gel. By this it is possible to avoid negative decrease of the concentration of active substance due to accumulation of the solvent which would impact the diffusion rate through the skin. Especially solvents based on water and/or alcohol are having at temperatures nearby the temperature of skin a vapor pressure which is sufficiently high to carry off the solvent by evaporation. However, the carrying off and/or diffusion rate of the solvent preferably is adjusted to the diffusion rate of the active substance through the skin to avoid accumulation of the solvent or precipitation of the active substance on the skin in a negative way.

According to the present invention a membrane which obstructs the transportation of the active substance e.g. due to a lower transfer rate than the skin can be successfully avoided and the achievable diffusion rate through the skin is therefore primarily only depending on the type of skin. Compared to conventional systems known from prior art it is possible to achieve higher diffusion rates and due to this only a smaller area of skin is necessary to absorb a certain amount of active substance.

The described invention offers the opportunity to precisely control the rate and the time pattern of systemic drug delivery. It can be applied to the delivery of drug into and/or across the skin. With the methodology according to the present invention the amount of active substance delivered per unit of time can be adjusted to values ranging between zero and a known maximum, the moments of time can be defined at which the delivery rate is set to a predetermined value and the delivery of drug over time spanning hours or days can be regulated in a programmed manner, e.g. using real time control. A device suitable to carry out the described technology offers the opportunity of fully automated transdermal drug delivery.

The method most widely used in prior art for automated controlled transdermal delivery is iontophoresis. With this method control of delivery of a drug is achieved by an electric current which is applied to the skin. By adjusting the current the delivery rate of the drug is regulated. Advantages of the present invention over iontophoresis are the ability to completely turn off delivery or reduce the delivery rate below a minimal value corresponding to passive skin permeation, the absence of skin irritation that the electric current may cause when applied to the skin and the low energy consumption compared to iontophoresis because normally no high currents are needed for extensive periods of time.

Conventional patch based delivery systems as known from prior art comprising a patch and a therewith interconnected dispensing unit are more or less suitable to administrate a chemical substance under a specific time regime, where the quantity of the specific dose delivered to the patch can be predetermined more or less accurate and each time period of dispensing the substance can be predetermined as well. However, turning delivery to a patch as known from prior art on and off causes uncontrolled time lag in the delivery rate to or through the skin. The delivery systems known from prior art often lead to a constantly diminishing dispensing rate. These problems are avoided by the present invention.

The disclosed invention offers a combination of formula dispensing with an on- and off-turning delivery of the formula and a simultaneous solvent recovery for the purpose of maintaining a constant and high drug delivery rate. The achievable delivery rate and the time lag due to on- and off-events result from the interplay between the rate of formula dispensing and the rate of solvent recovery. The former is preferably controlled by a freely programmable pump and the latter by amount and quality of the material of the solvent recovery element.

Precise control of delivery of the active substance is very important. Related thereto is the precise control of the solvent. The solvent may be controlled by additional means e.g. as described as follows.

A solvent removal system comprises a waste reservoir which is interconnected by a waste valve, e.g. a pinch valve, and/or a waste pump to the administration reservoir. In the case of a pin valve the waste valve preferably is driven by utilizing a wire made out of Shape-Memory-Alloy (SMA) or an alternative device pursuant to a pre programmed regimen. In a given example the waste valve is opened or the waste pump is turned on such that the solvent is removed and e.g. brought in contact to a desiccant such that the solvent is safely absorbed. Proper administration may be achieved by opening and closing the connection to the waste reservoir by an appropriate time regime. In certain applications it is helpful to switch the connection to the waste reservoir with a certain delay with respect to the administration of the active substance. Instead or in addition to a pinch valve a micro pump may be appropriate to pump excessive solvent into a waste reservoir. In a further embodiment the tubing e.g. for depletion of solvent can comprise absorbent material which thereby is brought into direct contact with depleted carrier solution. It is possible to remove depleted fluid either pursuant to a pre programmed profile or systematically, e.g. depleted fluid is brought into contact every 20 minutes with desiccant, by using a small lever or arm, or otherwise made to come into direct contact with the depleted carrier solution, resulting in absorption of the depleted carrier solution. Alternatively, a waste reservoir, e.g. a sponge, is lowered by a small lever or arm or otherwise to come into direct contact with the depleted carrier solution, resulting in immediate absorption of the depleted carrier solution. In a different embodiment a selectively permeable membrane surrounds a sponge or absorbent material, and the selectively permeable membrane primarily allows the solvent to pass through it (whether due to electric charge of the molecule or molecular size or acidity of the solvent vs. the drug or some other regulating means) and this semi permeable membrane either remains in constant contact with the diffusion surface or is periodically brought in to contact with the diffusion surface using an above described method. In a further embodiment a sponge or an absorbent material is in contact with the diffusion surface and a pretested and timed capillary action of the sponge is such that depleted carrier solution is absorbed at the right time and in proper amounts as to assist with the achievement of pre programmed dosage profiles, i.e. even though much active substance may be absorbed along with the carrier solution still sufficient drug is present to achieve the objectives.

Modulated dispensing of drug formula brings about a significant increase of delivery rate over the one-time addition of formula at equal drug concentration. Thus, maximization of drug delivery rate is achieved. This is because the removal of solvent from the relatively small dispensed volume creates in situ an increase of drug concentration with subsequent saturation and precipitation of drug in the interface in immediate contact with the skin as evidenced by dryness of the interface. By the herein described method it is possible that the delivery rate of the active substance can be adjusted using the same drug solution by changing the dispensed volume of solution. Depending on the field of application it was found that about 2 gram of desiccant are sufficient for trapping solvent over at least 9 hours when e.g. dispensing 40 µl/hr of a given drug formula. It was found that increase of drug concentration in the formula causes a corresponding increase of delivery rate for dispensing of e.g. 40 µl/hr but not for e.g. 15 µl/hr. Apparently, dryness of the interface for the latter dispensing volume is achieved far before each consecutive dispensing step, thus hampering drug permeation.

It was found that the dependency between delivery rate and dispensing volume is in general not linear but there exist optimal dispensing volume and frequency for maximal drug delivery. The found results are scalable for larger surface areas.

Possibilities to dispense a drug solution to at least one interface (administration device) may include a reservoir with an actuator such as a (micro)pump, a pressurized reservoir with a valve, a pressurized reservoir with a pump, a collapsible bag with a valve and/or a collapsible bag with a pump. Examples for appropriate pumps are a piezoelectric pump; an osmotic pump; an inkjet-like pump, a peristaltic pump, a pneumatic pump, a nebulizer pump, etc. Examples for valves are a pitch valve, a valve based on memory alloys, etc.

Depending on the field of application, solvent removal means may be for example: a desiccant in a bag, any other absorbent material in a bag, a desiccant/absorbent connected to the interface by a tube, a desiccant/absorbent connected to the interface by a tube which comprises a valve, a compartment connected to the environment for evaporation, a compartment through which gas is guided to promote evaporation, an absorbent sponge, an absorbent sponge attached to an arm that moves it to and away from the interface, an absorbent sponge with a gas blowing device for drying. The material surrounding the solvent removal means preferably is made out of tissue, cloth, membrane, etc. The administration device (compartment) may comprise, if appropriate, at least one sensor, e.g. a humidity sensor for feed back control to the dispenser.

For best results, the invention offers the opportunity to control and administer at least one active substance depending on the need defined by a certain therapy/target to be achieved. E.g. it is possible to slightly increase the dose over a certain period of time until a certain level is achieved. Then the administration of drug may be stopped, decreased in a certain manner or the administration of a further active substance may be overlaid or substituted by. If the therapy lasts more than (e.g.) one day it is possible to further adjust the dose administered depending on the time of the day or the physical behavior of the patient. Alternatively it is possible to deliver at first a higher dose of an active substance which is followed by a decrease and/or an increase and so on.

BRIEF DESCRIPTION OF THE DRAWINGS

FIG. 1 a first embodiment of a transdermal drug delivery system;

FIG. 2 a second embodiment of a transdermal drug delivery system;

FIG. 3 a third embodiment of a transdermal drug delivery system;

FIG. 4 three further embodiments of a drug delivery system according to the present invention.

DETAILED DESCRIPTION OF PREFERRED EMBODIMENTS

In the following the invention is explained in more detail on the basis of a few preferred embodiments. Same devices are indicated with same reference numbers. A person skilled in the art knows how to combine the different components shown in the different embodiments in a useful way.

FIG. 1 shows in a simplified manner a first embodiment of a dispensing system 1 for the non-invasive administration of at least one active substance 2 according to the present invention.

The dispensing system 1 comprises a dispensing unit 3 with a drug reservoir 5 for storing a liquid with at least one active substance 2. The reservoir 5 interconnects via pipes 4 to an administration device 6. To propel the active substance 2 from the reservoir 5 into the administration unit 6 the dispensing unit 3 comprises a propellant means, such as a pump 7 and/or the reservoir 5 may comprise a propellant gas and/or the active substance 2 is propelled in another way. In the herein shown simplified representation the control of the flow of the active substance (arrows 24) into the administration device 6 is accomplished by a pump 7 which is interconnected to a control unit 8 for precisely controlling delivery rate and the time pattern of the active substance administered. The control unit 8 can be or connected to a personal computer or any other suitable device, e.g. programmable by a touch screen and/or a keyboard and/or another user interface. In the herein described embodiment the control unit 8 is interconnected to an external unit 15, i.e. a microprocessor on a chip card or a computer unit connectable by a data connection 16 to the dispensing unit 3.

The administration unit 6 comprises an administration reservoir 9 which is interconnected by pipe 4 to the dispensing unit 3. The administration unit 6 is in the herein described embodiment attached to a surface of the skin 10 by a non-irritant adhesive layer 12 which acts as an interface device and is at least permeable for active substance contained in the administration chamber 9. Alternatively or in addition the administration device may be attached to the skin 11 in another way. If appropriate a membrane may be arranged between the administration reservoir 9 and skin 11 acting as interface device for transportation of the active substance (drug) into the skin or, depending on the field of application, the active substance may be applied direct onto the skin. The administration unit 6 comprises solvent recovery means 13 interconnected to the administration reservoir opposite to the adhesive layer 12. Between the solvent recovery means 13 and the administration reservoir 9 a separation means 14, here in the form of a layer, is located which is at least permeable for the solvent but preferably not for the active substance contained in the administration reservoir 9. In the shown embodiment the solvent recovery means 13 and the administration reservoir 9 are spaced apart a distance t by the separation means 14 such that direct contact is avoided between the solvent recovery means 13 and the active substance. In a preferred embodiment the solvent recovery means 13 and the administration reservoir 9 are separated by an air gap.

The liquid 2 stored in the drug reservoir 5 contains a sufficient amount of one or more active substances dissolved or dispersed at an appropriate concentration in a formulation which contains a solvent or a mixture of solvents which in general are more volatile then the active substance. If appropriate other excipients, for example tissue permeation promoters (enhancers), thickening substances, solubilizers, buffers, chemical stabilizers, preservatives may be present too. Alternatively or in addition the at least one active substance is dissolved or dispersed in a solvent outside the drug reservoir 5 before it is dripped into the administration reservoir 9 of administration unit 6. The formulation is dispensed by the dispensing unit 3 into the at least one administration reservoir 9, whereby volume and frequency of administration are controlled by the control unit 8. The volatile solvent evaporates from the administration reservoir 9 and is guided (indicated by first arrows 17) through a separation layer 14 to the solvent recovery means 13 where it is reclaimed or discharged. The active substance remains in the administration reservoir 9 and diffuses (indicated by second arrows 18) through an adhesive layer 12 into the skin 11. The solvent recovery means 13 serve to remove depleted solvent from the active area of the administration reservoir 9 such that the active substance concentration is maintained at a certain concentration and no unwanted substance is accumulated within the administration device 6. Upon quitting dispensing of formula into the administration device 6, the residual solvent is recovered and dryness of the interface is achieved, which results in controlled termination of drug delivery into skin 11. Normally the temperature of skin 11 is sufficient to evaporate and discharge the solvent. However, a heating element or other helping means may be used for supporting evaporation.

In general the active substance is completely enclosed in the administration/patch reservoir 9 of the administrative device 6 and is not in direct contact with the environment or other components. The administration device 6 may comprise interface means, e.g. comprising a membrane made out of a polymer, lined with a material, such as blotting paper, suitable to temporarily receive active substance, whereby the interface membrane is in functional contact with the surface 10 of the skin 11 to be treated. The drug formulation is dispensed onto the interface means by the dispensing unit 3.

The solvent recovery means 13 are normally arranged at a certain distance from the interface, the administration reservoir 9 respectively, is preventing uncontrolled absorption of solvent. The separation layer 14 may e.g. comprise or consist of an inert foam or an appropriate cellular material or honeycomb. The solvent recovery means 13 are preferably located within the administrative device 6 and preferably comprise one or more desiccants 23 and/or general or selective adsorbents 23 such as silica gel, molecular sieves or active carbon preferably surrounded by a non-wettable material permeable for the vapors of solvent, e.g. such as Gore-Tex®.

Subsequent the method will be described in a general manner: The drug formulation is dispensed into the administration reservoir 9 by the dispensing system 3. The volume and frequency of dispensing are freely programmable and are used to control the delivery rate and the time pattern of delivery of the chemical substance into the skin 11. The chemical substance is delivered from the administration reservoir 9 by diffusion in the skin 11 or onto the surface of the skin 10. The solvent recovery element 13 reclaims solvent that was dispensed with the formulation into the administration reservoir 9. The solvent recovery element is in close vicinity to but in general not in direct contact with the administration reservoir 9 to avoid uncontrolled absorption of solvent.

The volatile solvent evaporates from the interface under the influence of body heat and the vapors are trapped by the solvent recovery means 13, e.g. a chamber filled with absorbing material 23. The solvent recovery element 13 serves the purpose of removing depleted solvent from the patch reservoir 9 so that, after repeated dispensing, drug concentration maintains its highest value and no detrimental fluid (liquid) is accumulated within the administrating device 6. Upon quitting dispensing of drug formula, the residual solvent is recovered and dryness of the interface is achieved, which brings about stoppage of drug delivery.

By the pipe 4 fluid 2 comprising the active substance dissolved in a liquid dissolver is dosed into the administration device 6 either continuous or in portions. The administration device 6 solves the task to distribute the solution along the interface to the skin 11. In certain fields of application the administration device 6 can contain a material with capillary action preferably not so strong that the emission of active substance or dissolver is decisively hampered. At the most between skin 11 and administration device 6 a layer 12 of a skin compatible adhesive can be placed to allow a contact as good as possible between the administration device 6 and the surface of the skin 10. The dissolver in the administration device 6 in general is separated via a dissolver-permeable membrane which preferably is not extensively permeable for the at least one active substance. The separated dissolver reaches into a hollow space 13 which may be filled with a substance that absorbs the dissolver. Thereby the concentration of the dissolver in the region of the interface 12 may be kept below a certain level.

Figure 2:
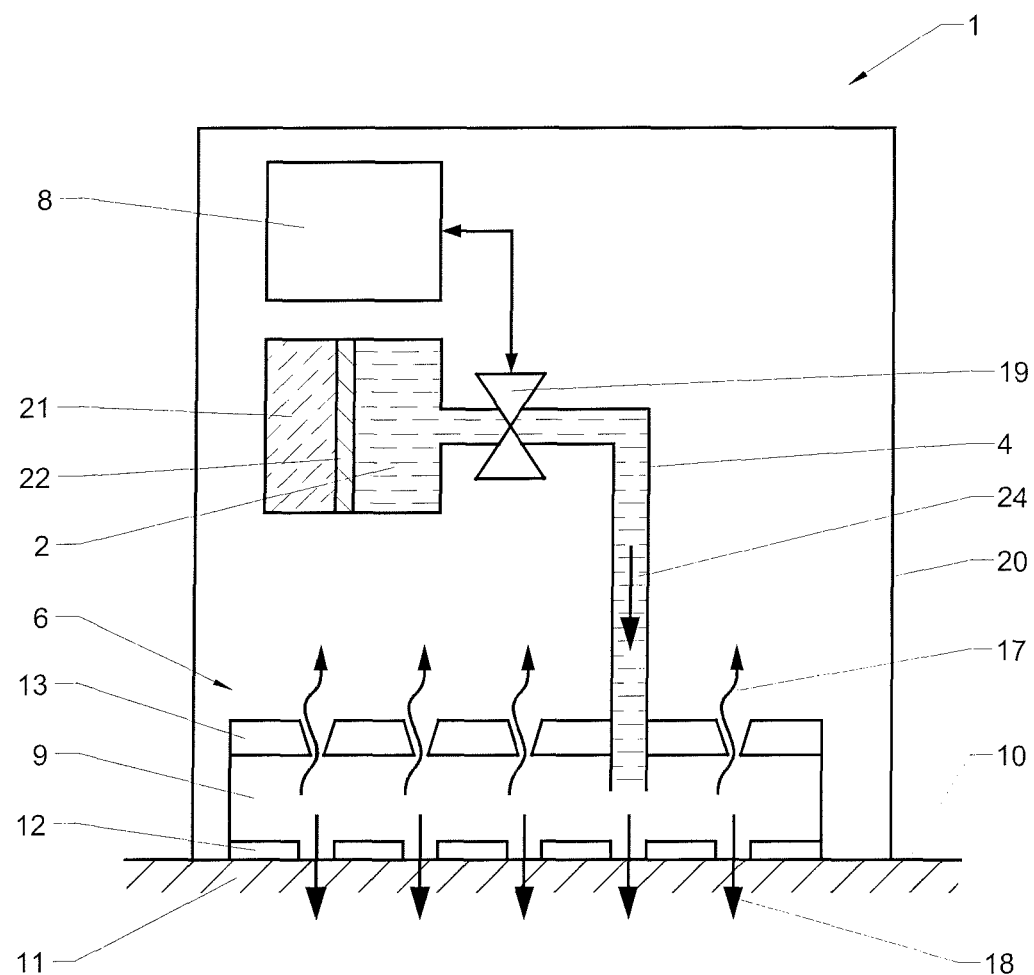

FIG. 2 is showing a further embodiment of a dispensing system 1 according to the present invention. The dispensing system 1 works in general similar to the one as described according to FIG. 1 and therefore only the differences are explained in more detail. In difference to FIG. 1 the reservoir 5 for the active substance 2 comprises a propellant gas 21 which is separated from the active substance 2 by a piston 22. The propellant gas 21 is under high pressure and thereby presses the active substance 2 through the pipe 4 into the administrative device 6. The flow (arrows 24) of the active substance 2 is controlled by the programmable control unit 8 via valve 19. The here shown device comprises an adhesive layer 12 whereby it is attached to the surface of the skin 10. As it can be seen the whole dispensing device 1 is incorporated as a portable device in a housing 20. The dispensing system 1 comprises a power source (not shown in detail) preferably in the form of a battery, e.g. foil battery or rechargeable battery. The dispensing device 1 may comprise control and programming means to control and program the device 1. Alternatively or in addition the device 1 may comprise an interface device such that it is connectable to an external data processing unit such as a computer or a laptop.

Compared to the device according to FIG. 1 the solvent recovery means 13 of the herein shown embodiment discharges the collected solvent into environment by evaporation 17. This offers the opportunity that no depleted solvent has to be collected separately. Depending of the environmental condition outside the administration device 6 the diffusion rate of the active substance into the skin may be influenced.

Figure 3:
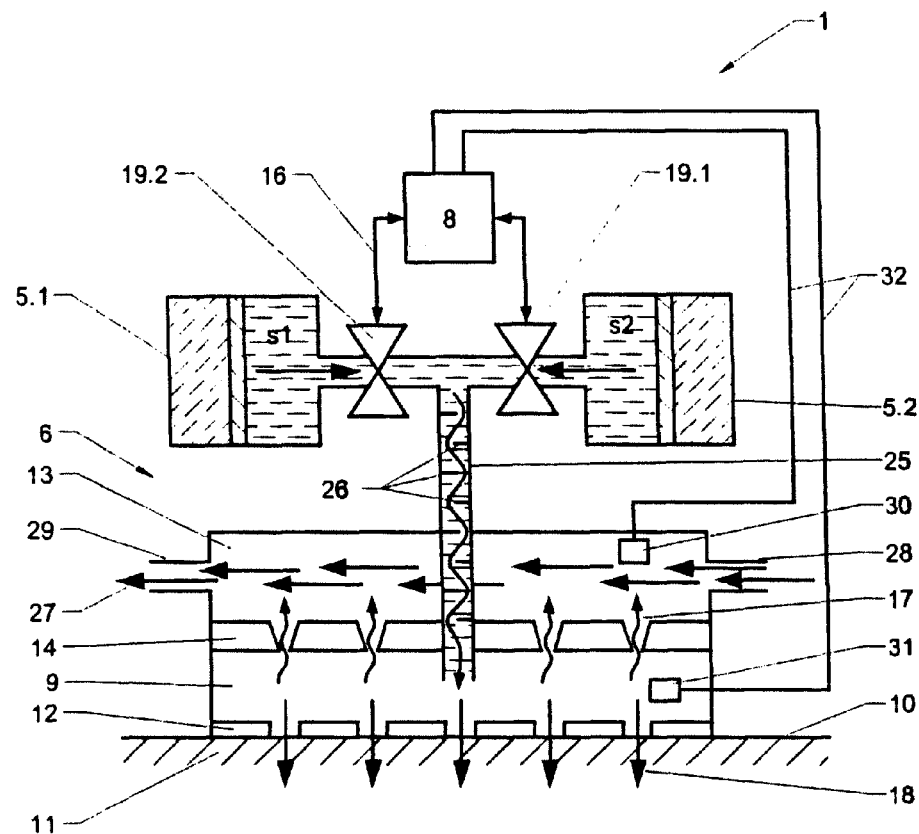

FIG. 3 is showing a third embodiment of a dispensing system 1. A first and a second active substance sl, s2 is stored in a first and a second reservoir 5.1, 5.2. The flow (indicated by arrows) of the first and the second fluid sl, s2 into a connecting pipe 25 is controlled by a first and a second valve 19.1, 19.2, as described above interconnected, to a programmable flow control device 8. The connecting pipe 25 may comprise mixing means 26 such as impellers or vortex means providing an appropriate preparation of mixture of the active substances sl, s2. This offers the opportunity to administer drugs which cannot be stored together due to incompatibility or another reason. Alternatively or in addition the bringing together of several active substances may take place in the administration chamber 9 of the administration device 6. The solvent absorption chamber 13 is separated by separation means 14 in the described manner from the administration chamber 9. The separation means 14 are made such that solvent is preferably absorbed by evaporation (indicated by arrows 17). In the shown embodiment the evaporation rate is controlled/adjusted by a fluid stream (indicated by arrows 27), preferably air, which is guided into the solvent absorption chamber 13 by an inlet 28 and exits by an outlet 29. The condition of the administration device and the absorption of the at least one active substance into the skin 11 as indicated by arrows 18, may be controlled by sensors 30, 31 interconnected to the control device 8 by data connections 32. The sensors of the herein described embodiment are arranged in the administration chamber 9 and the solvent absorption chamber 13 such that the administration of the at least one active substance and/or the absorption of the at least one solvent may be controlled. Depending on the field of application, the sensors 30, 31 are suitable to measure relevant parameters such as temperature and/or humidity and/or pressure and/or concentration.

The drug formulation is dispensed into the administration reservoir 9 via a connecting pipe 25. The volume and frequency of active substance discharged by the reservoirs 5.1, 5.2 is herein freely programmable and suitable to control the delivery rate and the time pattern of delivery of the at least one chemical substance to the patient.

By the connecting pipe 25 active substance dissolved in a liquid dissolver is dosed into the administration device 6 either continuous or in portions. Between skin 11 and administration chamber 9 a porous layer 12 is arranged in general having a higher transfer rate then the skin 11.

Solvent delivered with the active substance is absorbed by the solvent recovery chamber 13 and carried away by the fluid stream 27. The solvent recovery element 13 serves the purpose of removing solvent from the patch reservoir 9 so that, after repeated dispensing, drug concentration maintains its value and no detrimental fluid (liquid) is accumulated within the administrating device 6. Upon quitting the dispensing of drug formula, the residual solvent is recovered and dryness of the interface is achieved in a defined manner. Quick stop of the administration may be achieved by flushing the device 6, respectively the administration reservoir 9, by an appropriate fluid containing no active substance, e.g. air, and/or detergent. A separate piping with adequate reservoirs pumps and valves may be foreseen for that purpose, preferably interconnected to the control device 15. In the shown embodiment it is possible to store a fluid s1 comprising at least one active substance in the first reservoir 5.1 and a solvent s2 in the second reservoir 5.2. This offers the opportunity to determine the concentration of active substance s1 in the solvent s2 depending on given need. By this it is also possible to flush the administration device 6 by solvent s2 e.g. to bring administration of active substance to a quick stop. Additional means for carrying off of the flush may be foreseen.

Figure 4:
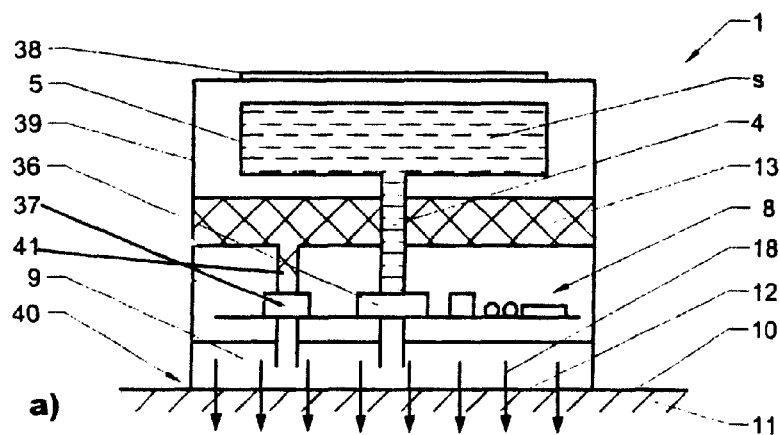
Figure 4:
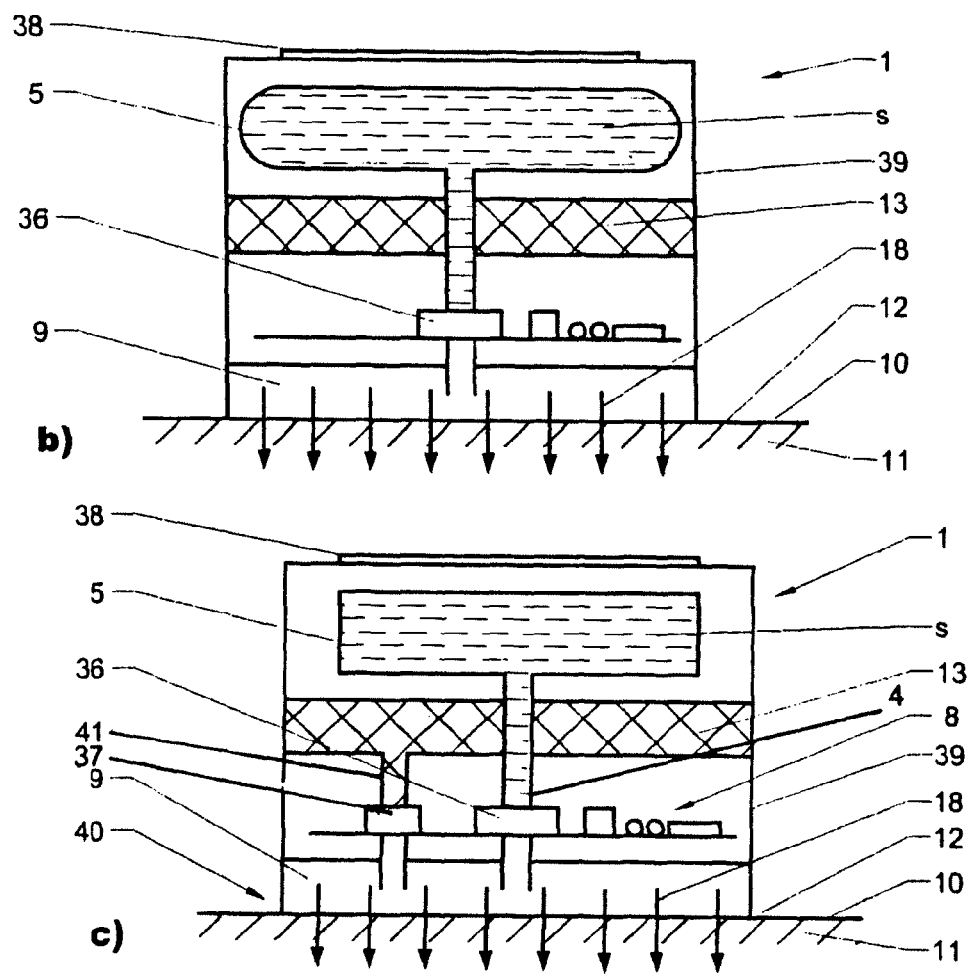

FIGS. 4 *a*) to *c*) are showing three further embodiment of a dispensing system 1 for administration of at least one active substance s. The dispensing systems 1 according to FIGS. 4 *a*) to 4 *c*) have in general a similar set up comprising an outer housing 39 with a display 38 interconnected to a programmable control unit 8. The lower surface of the devices 1 serves as footstep 40 while in use on a porous surface 10 and comprises an interface 12 for transferring active substance to a skin 11 through the porous surface 10. Inside the housing 39 the devices 1 comprise a drug reservoir 5 for at least one active substance s. The drug reservoir 5 is preferably a collapsible bag or a pressurized compartment due to internal or external pressure suitable to expel active substance into the administration chamber 9 via a pipe 4 which interconnects the drug reservoir 5 with the administration reservoir 9. In use the administration reservoir 9 is fluidly interconnected to the porous surface 10 of skin 11 such that active substance s dispensed into the administration chamber 9 may pass into skin 11 as indicated by arrows 18. The flow of the active substance s is controlled by a first valve and/or a pump 36 which is logically interconnected to the control unit 8 which controls the administration of active substance s according to a preset regime. A solvent recovery means 13 is used to remove depleted solvent from the administration chamber 9 by waste pipe 41. If administration of the active substance needs to be stopped it is possible to pump active substance from the administration chamber back into the drug reservoir 5 or the connecting pipe 4 by pump 36.

In the dispensing device 1 according to FIG. 4 *a*) a pressurized drug reservoir 5 is interconnected with a tube or pipette 4. A pinch valve 36 and an SMA driven wire opens and closes the valve 36 according to a preprogrammed regimen. At inception of delivery of active substance valve 36 is opened to release the active substance pipe 4 onto the membrane of the interface device 12 which is in functional contact with the skin 11. A second valve 37 controls the removal of depleted solvent into the waste reservoir of the solvent removal means 13.

FIG. 4*b*) shows a dispensing device 1 with a collapsible drug reservoir 5 which is used in conjunction with a tube or pipette 4 and a micro pump 36 preprogrammed to dispense onto interface 12. The micro pump 36 is interconnected to control unit 8 which controls administration of the active substance s. Depleted solvent is in the present embodiment absorbed from the administration chamber 9 by a waste reservoir 13 filled with hydrophilic substance.

The embodiment of FIG. 4*c*) comprises a pressurized drug reservoir 5 in conjunction with a tube or pipette 4, a micro pump 36 controlled by control unit 8 pre-programmed to dispense and start pumping active substance s onto diffusion surface 12. A second pinch valve and/or micro pump 37 interconnects the administration chamber 9 with the waste reservoir 13. The micro pump 37 either pumps solution into the waste reservoir 13 and/or the valve 37 opens and depleted carrier solution is absorbed into the waste reservoir 13.

It is obvious to one skilled in the art that, without leaving the scope of the invention, further embodiments may be achieved by combination of features of the herein described embodiments.

What is claimed is:

1. A device for transdermal administration of at least one active substance to a porous surface, comprising:
   (a) an administration reservoir;
   (b) a dispensing device interconnected to the administration reservoir for delivery of at least one active substance dissolved in a solvent to the administration reservoir, wherein the administration reservoir is suitable to receive the active substance dissolved in the solvent;
   (c) an interface configured to contact the porous surface and suitable for transferring the active substance from the administration reservoir to the porous surface; and
   (d) a solvent removal element configured to absorb solvent from the administration reservoir by evaporation when the interface is in contact with the porous surface, wherein the solvent removal element does not remove the active substance, and wherein the solvent removal element is not in contact with the interface;
   wherein the transfer of the active substance from the administration reservoir to the porous surface is controlled via the absorption of solvent by the solvent removal element.

2. The device according to claim 1 wherein the interface is suitable to be arranged in vicinity to the porous surface.

3. The device according to claim 2 wherein the interface comprises an adhesive surface suitable to be attached to the porous surface.

4. The device according to claim 1 wherein the interface is a membrane permeable for the active substance.

5. The device according to claim 1 wherein the solvent removal element is separated from the administration reservoir by a separation means.

6. The device according to claim 5 wherein the separation means is selected from the group consisting of a membrane, a foam, a cellular material, a honeycomb, and an air gap.

7. The device according to claim 5 wherein the administration reservoir and the solvent removal element are spaced apart a distance by the separation means.

8. The device according to claim 1 wherein the solvent removal element comprises one or more of the following materials: Desiccant, general or a selective absorbent material, silica gel, a molecular sieve, and active carbon.

9. The device according to claim 1 wherein the dispensing device comprises at least one reservoir for an active substance which is interconnected to the administration reservoir.

10. The device according to claim 9 wherein the dispensing device comprises a propellant means to propel the active substance from the one reservoir into the administration reservoir.

11. The device according to claim 10 wherein the propellant means is a pump and/or a propellant gas.

12. The device according to claim 9 wherein the dispensing device comprises a first reservoir comprising a first active substance and a second reservoir comprising a second active substance and the first and the second active substance are mixed by mixing means before delivery to the administration reservoir.

13. The device according to claim 12 wherein the mixing means is a pipe with vortex means providing an appropriate preparation of mixture.

14. The control device according to claim 1 wherein the administration of the active substance is controlled by a control device.

15. The device according to claim 14 wherein the control device is programmable according to a predetermined regime or time pattern or interval of administration of the at least one active substance.

16. The device according to claim 14 wherein the control device is interconnected with at least one sensor for measuring a condition of the at least one active substance within the administration reservoir.

17. The device according to claim 16 wherein the administration of the active substance is based on the signal of the at least one sensor.

18. The device according to claim 14 wherein the control device is interconnected to at least one valve for controlling the administration of the at least one active substance.

19. The device of claim 1 wherein the solvent removal element controls the transfer of the active substance from the administration reservoir to the porous surface by controlling the concentration of the at least one active substance in the administration reservoir.

20. The device of claim 1 wherein the solvent removal element controls termination of the transfer of the active substance from the administration reservoir to the porous surface by drying the interface.

21. The device of claim 1, further comprising a housing, wherein the administration reservoir, the dispensing device, and the solvent removal element are located within the housing.

22. The device of claim 1, wherein the solvent removal element comprises an evaporation means.

23. The device of claim 1, wherein the solvent removal element comprises a heating element for supporting evaporation.

24. The device of claim 1, wherein the solvent removal element comprises a compartment through which gas is guided to promote evaporation.

25. The device of claim 1, wherein the solvent removal element comprises a hydrophilic substance.

* * * * *